United States Patent [19]

Taguchi et al.

[11] Patent Number: 4,729,995
[45] Date of Patent: Mar. 8, 1988

[54] PYRIMIDINE 2,4-DIOXAMATE COMPOUNDS AND PHARMACEUTICAL COMPOSITIONS

[75] Inventors: Hiroaki Taguchi, Ibaraki; Takeo Katsushima, Kyoto; Masakazu Ban, Mukoh; Shoichi Aoki, Hino; Akihiko Watanabe, Otsu, all of Japan

[73] Assignee: Toyo Boseki Kabushiki Kaisha, Osaka, Japan

[21] Appl. No.: 33,734

[22] Filed: Apr. 3, 1987

[30] Foreign Application Priority Data

Apr. 21, 1986 [JP] Japan .................................. 60-91482
Nov. 22, 1986 [JP] Japan ................................. 60-279040

[51] Int. Cl.$^4$ ................ A61K 31/505; A61K 31/535; C07D 239/48; C07D 413/04
[52] U.S. Cl. .................................... 514/212; 514/233; 514/234; 514/236; 514/252; 514/272; 514/275; 540/601; 540/467; 540/470; 540/481; 544/122; 544/295; 544/320; 544/321; 544/323
[58] Field of Search .............. 540/601, 467, 470, 481; 544/122, 323, 295, 320, 321; 514/212, 233, 234, 236, 252, 272, 275

[56] References Cited

PUBLICATIONS

Bazzano, International Publication Number WO86/00616, Jan. 30, 1986.

Primary Examiner—Robert W. Ramsuer
Attorney, Agent, or Firm—Wegner & Bretschneider

[57] ABSTRACT

Novel pyrimidine compounds of the formula:

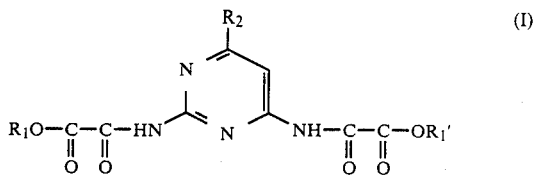

wherein $R_1$ and $R_1'$ are each hydrogen atom, a lower alkyl, benzyl, an alkali metal, or ammonium; $R_2$ is hydrogen atom, a halogen atom, a lower alkyl, a lower alkoxy, an aryl, a group of the formula:

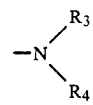

(wherein $R_3$ and $R_4$ are each hydrogen atom, a lower alkyl, or an aryl), or a group of the formula:

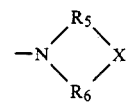

[wherein $R_5$ and $R_6$ are each an alkylene having 1 to 3 carbon atoms, and X is oxygen atom, methylene, or a group of the formula: >N-Y (wherein Y is hydrogen atom, a lower alkyl, benzyl, or an aryl)], which have excellent antiallergic activities and are useful for the prophylaxis and treatment of various allergic diseases, and a pharmaceutical composition containing said pyrimidine compound as an active ingredient.

6 Claims, No Drawings

PYRIMIDINE 2,4-DIOXAMATE COMPOUNDS AND PHARMACEUTICAL COMPOSITIONS

This invention relates to novel pyrimidine compounds having excellent antiallergic activities and being useful as an antiallergic agent. More particularly, it relates to pyrimidine compounds of the formula:

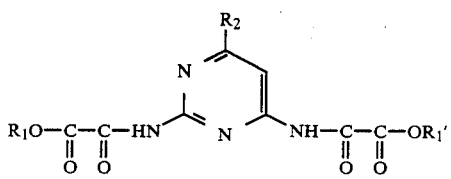

wherein $R_1$ and $R_1'$ are the same or different and are each hydrogen atom, a lower alkyl, benzyl, an alkali metal, or ammonium; $R_2$ is hydrogen atom, a halogen atom, a lower alkyl, a lower alkoxy, an aryl, a group of the formula:

(wherein $R_3$ and $R_4$ are the same or different and are each hydrogen atom, a lower alkyl, or an aryl), or a group of the formula:

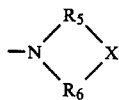

[wherein $R_5$ and $R_6$ are the same or different and are each an alkylene having 1 to 3 carbon atoms, and X is oxygen atom, methylene, or a group of the formula: $>N-Y$ (wherein Y is hydrogen atom, a lower alkyl, benzyl, or an aryl)], or a hydrate thereof, which have excellent antiallergic activities and are useful for the prophylaxis and treatment of various allergic diseases, and a pharmaceutical composition containing said pyrimidine compound as an active ingredient.

PRIOR ART

There have hitherto been studied various compounds which are useful for the prophylaxis and treatment of various allergic diseases, and some antiallergic agents have already been commercially available. Among the allergic diseases, bronchial asthma, urticaria, allergic rhinitis, etc. are an immediate allergy which is classified as type I allergy.

The type I allergy is further classified into three stages in accordance with the mechanism of allergic response and the acting region of antiallergic agent. That is, at the first stage, when a foreign antigen invades into the body, IgE antibody against the antigen is produced by mutual action of macrophage, T cells and B cells, and the IgE antibody is fixed onto IgE receptor of mastocytes or basocytes in the tissues and thereby sensitization is induced.

Subsequently, a foreign antigen invades again into the body, and then the foreign antigen is bound with the IgE fixed onto the IgE receptor of cells, and the antigen-antibody reaction induces activation of enzymes in cell membrane and influx of calcium ion into cells, which induce further biochemical changes such as enzymatic reaction, or histomorphological changes such as degranulation. As the result, chemical mediators such as histamine or SRS-A (=slow reacting substance of anaphylaxis) are released from the cells. This stage is called as the second stage.

The chemical mediators released from the cells in the above second stage induce contracture of smooth muscle, promotion of capillary permeation, or promotion of secretion, and thereby, various allergic symptoms are induced. This stage is called as the third stage.

Among the known antiallergic agents, antibody-producing inhibitors act at the first stage, and antihistaminic agents act at the third stage. As the medicament acting on the second stage, there are known DSCG (=disodium chromoglycate) and Tranilast.

BRIEF DESCRIPTION OF THE INVENTION

The present inventors have intensively studies as to a medicament which can show excellent antiallergic activity against the allergic symptoms at the second stage as mentioned above, and have found that specific pyrimidine compounds show excellent inhibitory activities on the release of chemical mediators such as histamine and SRS-A.

An object of the invention is to provide novel pyrimidine compounds which are useful for the prophylaxis or treatment of various allergic diseases induced by chemical mediators. Another object of the invention is to provide a pharmaceutical composition containing as an active ingredient the pyrimidine compound as set forth above. These and other objects and advantages of the invention will be apparent to those skilled in the art from the following description.

DETAILED DESCRIPTION OF THE INVENTION

The pyrimidine compounds of this invention have the formula (I) as set forth hereinbefore.

Among the groups for $R_1$ and $R_1'$ in the formula (I), the lower alkyl group includes straight chain or branched chain alkyl groups having 1 to 6 carbon, preferably methyl, ethyl, n-propyl, or isopropyl; the alkali metal includes sodium and potassium; the ammonium includes ammoniums derived from ammonia or non-toxic amines such as triethylamine, n-propylamine, n-butylamine, $NH_2C(CH_2OH)_3$, etc.

Among the groups for $R_2$, the halogen atom includes fluorine, chlorine, bromine or iodine; the lower alkyl group includes straight chain or branched chain alkyl group having 1 to 6 carbon atoms, preferably methyl; the lower alkoxy group includes straight chain or branched chain alkoxy groups having 1 to 6 carbon atoms, preferably methoxy; the aryl group includes phenyl, tolyl, naphthyl, pyridyl, pyrimidinyl, etc.

Among the groups for $R_3$ and $R_4$, the lower alkyl group includes straight chain or branched chain alkyl groups having 1 to 6 carbon atoms, the aryl group includes phenyl, tolyl, naphthyl, pyridyl, pyrimidinyl, etc.

Among the groups for Y, the lower alkyl group includes straight chain or branched chain alkyl groups having 1 to 6 carbon atoms; the aryl group includes phenyl, tolyl, naphthyl, pyridyl, pyrimidinyl, etc.

Preferred $R_2$ group is the group of the formula:

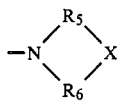

(wherein $R_5$, $R_6$ and X are as defined above), particularly a member selected from the group consisting of piperidino, homopiperidino, pyrrolidino, morpholino, and 4-methylpiperazino groups.

The pyrimidine compounds (I) of this invention can be prepared by various processes.

For example, the compounds (I) can be prepared by reacting a 2,4-diaminopyrimidine of the formula (II):

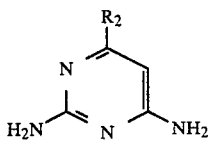

wherein $R_2$ is as defined above, with an acid chloride of the formula (III):

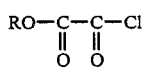

wherein R is a lower alkyl or benzyl.

The above reaction can be carried out in an inert solvent, such as pyridine and the like. The reaction may proceed without heating, but may be carried out by heating in order to ensure the completion thereof, for example at a temperature of from room temperature to a reflux temperature for 0.5 to 5 hours.

Alternatively, the compounds (I) of this invention can be prepared by reacting the above-mentioned 2,4-diaminopyrimidine (II) with a dialkyl oxalate of the formula (IV):

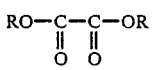

wherein R is as defined above, in a solvent (e.g. pyridine, etc.) at a temperature of from room temperature to a reflux temperature for 0.5 to 5 hours.

The oxaminic acid esters thus obtained may be converted into other esters by an ester exchange reaction, into dibasic carboxylic acids by hydrolysis thereof, or into alkali metal salts or ammonium salts thereof by conventional methods.

The compounds of this invention exhibit excellent inhibitory activity against release of chemical mediators and antiallergic activity as is shown by the following Experiments.

EXPERIMENT 1

Hartley guinea pig (male, weighing about 400 g) was passively sensitized by an intravenous injection of anti-egg albumin guinea pig serum. 48 hours after the sensitization, the lung was taken out and cut finely to prepare a lung suspension. To the suspension were added a test compound and egg albumin, and the mixture was incubated at 37° C. After the reaction, the mixture was centrifuged, and then the amount of histamine and SRS-A in the supernatant was measured. The amount of histamine was measured by a fluorometry in accordance with the method of May et al [cf. J. Allerg., Vol. 40, page 12 (1970)]. The amount of SRS-A was measured by a bioassay using an isolated guinea pig ileum. That is, the guinea pig ileum was suspended within Magnus vessel, and thereto were added an antihistaminic, an antiacetylcholine agent and a test solution, and based on the shrink of guinea pig ileum, the amount of SRS-A was calculated. The inhibitory rate of the compounds of this invention against release of histamine and SRS-A is shown in Table 1.

TABLE 1

| Test compounds | Concentration of compound ($\mu$M) | Release inhibitory rate (%) | |
|---|---|---|---|
| | | Histamine | SRS-A |
| Dimethyl 6-piperidino-pyrimidine-2,4-dioxamate | 100 | 12.2 | 46.6 |
| Dimethyl 4-chloro-pyrimidine-2,6-dioxamate monohydrate | 100 | 24.5 | 52.7 |
| Dimethyl 6-methoxy-pyrimidine-2,4-dioxamate monohydrate | 100 | 44.2 | 57.6 |
| Dimethyl 6-morpholino-pyrimidine-2,4-dioxamate | 100 | 36.2 | 52.6 |
| Dimethyl 6-pyrrolidino-pyrimidine-2,4-dioxamate | 100 | 16.1 | 32.8 |
| Dimethyl 6-piperidino-pyrimidine-2,4-dioxamate | 100 | 32.1 | 50.0 |
| Dimethyl 6-morpholino-pyrimidine-2,4-dioxamate | 100 | 27.7 | 47.3 |
| Dimethyl 6-pyrrolidino-pyrimidine-2,4-dioxamate | 100 | 19.9 | 40.2 |
| Dimethyl 6-homopiperidinopyrimidine-2,4-dioxamate | 100 | 26.3 | 49.2 |
| Diisopropyl 6-morpholinopyrimidine-2,4-dioxamate | 100 | 30.8 | 59.9 |
| Di-n-propyl 6-piperidinopyrimidine-2,4-dioxamate | 100 | 31.6 | 52.3 |
| Di-n-propyl 6-morpholinopyrimidine-2,4-dioxamate | 100 | 29.8 | 50.0 |
| Dibenzyl 6-piperidino-pyrimidine-2,4-dioxamate semihydrate | 100 | 26.5 | 48.6 |
| Dibenzyl 6-morpholino-pyrimidine-2,4-dioxamate | 100 | 31.1 | 52.6 |
| Diethyl 6-(4-methylpiperazino)pyrimidine-2,4-dioxamate | 100 | 23.7 | 33.3 |
| 6-Piperidinopyrimidine-2,4-dioxamic acid monohydrate | 100 | 20.5 | 43.2 |
| 6-Morpholinopyrimidine-2,4-dioxamic acid monohydrate | 100 | 21.2 | 47.3 |

EXPERIMENT 2

Wistar rats (male, weighing about 200 g) were passively sensitized by an intradermal injection of each 0.1 ml of anti-egg albumin rat serum both sides of median line on back of the animals (each two points, totally 4 points). After 48 hours, a mixture (1 ml) of egg albumin and Evans blue was injected via tail vein, by which PCA (passive cutaneous anaphylaxis) was induced.

After 30 minutes, the blue colored region was cut out and the amount of color was measured by the method of Katayama et al [cf. Microbiol. Immunol., Vol. 22, page 89 (1978)]. One hour before the induction of PCA, each test compound was orally administered to six rats at a dose of 200 mg/kg per each rat. The PCA inhibitory rate is shown in Table 2.

TABLE 2

| Test compounds | PCA inhibitory rate (%) |
|---|---|
| Diethyl 6-piperidinopyrimidine-2,4-dioxamate | 92.4 |
| Diethyl 4-chloropyrimidine-2,6-dioxamate monohydrate | 41.7 |
| Diethyl 6-methoxypyrimidine-2,4-dioxamate monohydrate | 83.4 |
| Diethyl 6-morpholinopyrimidine-2,4-dioxamate | 96.6 |
| Diethyl 6-pyrrolidinopyrimidine-2,4-dioxamate | 87.3 |
| Dimethyl 6-piperidinopyrimidine-2,4-dioxamate | 85.6 |

In the above experiments, the test compound was orally administered to six rats at a dose of 30 mg/kg per each rat one hour before the antigen challenge. PCA inhibitory rate is shown in Table 3.

TABLE 3

| Test compounds | PCA inhibitory rate (%) |
|---|---|
| Dimethyl 6-morpholinopyrimidine-2,4-dioxamate | 98.5 |
| Dimethyl 6-pyrrolidinopyrimidine-2,4-dioxamate | 81.2 |
| Dimethyl 6-homopiperidinopyrimidine-2,4-dioxamate | 76.9 |

In the above experiments, the test compound was orally administered to six rats at a dose of 30 mg/kg per each rat 30 minutes before the antigen challenge. The PCA inhibitory rate is shown in Table 4.

TABLE 4

| Test compounds | PCA inhibitory rate (%) |
|---|---|
| Diethyl 6-piperidinopyrimidine-2,4-dioxamate | 90.6 |
| Diethyl 6-morpholinopyrimidine-2,4-dioxamate | 91.7 |
| Diethyl 6-pyrrolidinopyrimidine-2,4-dioxamate | 73.1 |
| Dimethyl 6-piperidinopyrimidine-2,4-dioxamate | 54.4 |

In the above experiments, the test compound was intravenously administered to six rats at a dose of 3 mg/kg per each rat 5 minutes before the antigen challenge. The PCA inhibitory rate is shown in Table 5.

TABLE 5

| Test compounds | PCA inhibitory rate (%) |
|---|---|
| Diethyl 6-piperidinopyrimidine-2,4-dioxamate | 100 |
| Dimethyl 6-morpholinopyrimidine-2,4-dioxamate | 100 |
| Diisopropyl 6-morpholinopyrimidine-2,4-dioxamate | 100 |
| 6-Piperidinopyrimidine-2,4-dioxamic acid monohydrate | 100 |
| 6-Morpholinopyrimidine-2,4-dioxamic acid monohydrate | 100 |

The compounds of this invention can be administered by oral, parenteral, or inhalation route, preferably by oral route. The compounds can be used in the form of a conventional pharmaceutical preparation in admixture with a conventional pharmaceutically acceptable carrier or diluent. For example, preparations for oral administration include tablets, capsules, granules, fine granules, syrups, powders, and the like. The preparations for parenteral administration include aqueous solution for intravenous injection, oily suspension for intramuscular injection, and the like. They can also be administered with an inhalator in the form of an aerosol spray or dried powder so that the compound can directly contact with the lung.

Dose of the compounds of this invention may vary depending on the kinds of diseases, the age, weight and sex of the patient, the administration routes, etc., but is usually administered in the range of 2 to 2,000 mg per day in adult. The dose may be divided and administered in two to several times per day.

The compounds of this invention are illustrated by the following Examples, but should not be construed to be limited thereto.

EXAMPLE 1

Preparation of diethyl 6-piperidinopyrimidine-2,4-dioxamate:

2,4-Diamino-6-piperidinopyrimidine (3.86 g) is dissolved in anhydrous pyridine (15 ml) and thereto is added dropwise ethyloxalyl chloride (6.6 g) under ice cooling, and the mixture is stirred at room temperature for one hour. To the reaction mixture is added water, and the mixture is extracted with ethyl acetate. The organic layer is washed with water and saturated aqueous sodium chloride, dried over anhydrous sodium sulfate and concentrated under reduced pressure. The resulting solid is recrystallized from ethyl acetate-n-hexane to give title compound (5.2 g) having the following physical properties.

m.p. 145°–147° C.

IR (KBr) $\nu$: 3425, 3020, 2925, 2880, 1725, 1695, 1620, 1560, 1520, 1440, 1380, 1315, 1220, 1085, 1045, 1000, 885, 860, 815 cm$^{-1}$.

NMR (DMSO-$d_6$) $\delta$: 10.90 (1H, s), 10.16 (1H, s), 6.95 (1H, s), 4.27 (2H, q), 4.23 (2H, q), 3.70–3.15 (4H, m), 1.80–1.20 (6H, m), 1.30 (3H, t), 1.23 (3H, t).

Elementary analysis: Calcd.: C, 51.90; H, 5.89; N, 17.80 (%). Found: C, 52.16; H, 5.85; N, 17.89 (%).

EXAMPLE 2

Preparation of diethyl 4-chloropyrimidine-2,6-dioxamate monohydrate:

4-Chloro-2,6-diaminopyrimidine (2.88 g) is dissolved in anhydrous pyridine (20 ml) and thereto is added dropwise ethyloxalyl chloride (6.01 g) under ice cooling, and the mixture is stirred at room temperature for 2 hours. To the reaction mixture is added water, and the precipitated solid is separated by filtration and recrystallized from ethanol to give title compound (4.6 g) having the following physical properties.

m.p. 172°–173° C.

IR (KBr) $\nu$: 3610, 3330, 2980, 1720, 1590, 1540, 1515, 1420, 1360, 1295, 1240, 1195, 1165, 1120, 1040, 1005, 900, 840 cm$^{-1}$.

NMR (DMSO-$d_6$) $\delta$: 11.5–10.3 (2H), 7.69 (1H, s), 4.30 (4H, q), 1.30 (3H, t), 1.27 (3H, t).

Elementary analysis: Calcd.: C, 39.73; H, 4.17; N, 15.45; Cl, 9.78 (%). Found: C, 39.73; H, 4.13; N, 15.41; Cl, 9.83 (%).

EXAMPLE 3

Preparation of diethyl 6-methoxypyrimidine-2,4-dioxamate monohydrate:

2,4-Diamino-6-methoxypyrimidine (3.78 g) is dissolved in anhydrous pyridine (20 ml) and thereto is added dropwise ethyloxalyl chloride (9.83 g) under ice cooling, and the mixture is stirred at room temperature for one hour. To the reaction mixture is added water, and the mixture is extracted with ethyl acetate. The organic layer is washed with water and saturated aqueous sodium chloride, dried over anhydrous sodium sulfate and concentrated under reduced pressure. The resulting solid is recrystallized from water-ethanol to give title compound (8.8 g) having the following physical properties.

m.p. 132°–134° C.

IR (KBr) $\nu$: 3625, 3530, 3420, 3010, 1740, 1610, 1530, 1475, 1400, 1305, 1210, 1170, 1100, 1050, 1015, 970, 840 cm$^{-1}$.

NMR (DMSO-$d_6$) $\delta$: 11.30 (1H, s), 10.60 (1H, s), 7.03 (1H, s), 4.29 (4H, q), 3,87 (3H, s), 1.30 (3H, t), 1.25 (3H, t).

Elementary analysis: Calcd.: C, 43.58; H, 5.06; N, 15.64 (%). Found: C, 43.75; H, 4.85; N, 15.89 (%).

EXAMPLE 4

Preparation of diethyl 6-morpholinopyrimidine-2,4-dioxamate:

2,4-Diamino-6-morpholinopyrimidine (2.41 g) is dissolved in anhydrous pyridine (14 ml) and thereto is added dropwise a solution of ethyloxalyl chloride (3.71 g) in toluene (5 ml) under ice cooling, and the mixture is stirred at room temperature for 30 minutes. To the reaction mixture is added water, and the mixture is extracted with ethyl acetate. The organic layer is washed with water and saturated aqueous sodium chloride, dried over anhydrous sodium sulfate and concentrated under reduced pressure. The resulting solid is recrystallized from ethyl acetate-ethanol to give title compound (1.91 g) having the following physical properties.

m.p. 169°–170° C.

IR (KBr) $\nu$: 3430, 3410, 3000, 2970, 2910, 2870, 1730, 1610, 1580, 1510, 1440, 1380, 1310, 1280, 1260, 1210, 1160, 1120, 1040, 1010, 980, 950, 890, 860, 810, 780, 680, 630, 600, 530 cm$^{-1}$.

Elementary analysis: Calcd.: C, 48.61; H, 5.33; N, 17.71 (%). Found: C, 48.70; H, 5.27; N, 17.43 (%).

EXAMPLE 5

Preparation of diethyl 6-pyrrolidinopyrimidine-2,4-dioxamate:

In the same manner as described in Example 1 by using 2,4-diamino-6-pyrrolidinopyrimidine (3.00 g) and ethyloxalyl chloride (5.03 g), there is prepared title compound (3.12 g) having the following physical properties.

m.p. 171°–172° C.

IR (KBr) $\nu$: 3410, 3330, 2980, 2870, 1720, 1610, 1560, 1520, 1420, 1370, 1350, 1300, 1270, 1190, 1150, 1040, 1010, 810 cm$^{-1}$.

Elementary analysis: Calcd.: C, 50.66; H, 5.58; N, 18.46 (%). Found: C, 50.78; H, 5.57; N, 18.26 (%).

EXAMPLE 6

Preparation of dimethyl 6-piperidinopyrimidine-2,4-dioxamate:

2,4-Diamino-6-piperidinopyrimidine (5.8 g) is dissolved in anhydrous pyridine (80 ml) and thereto is added dropwise methyloxalyl chloride (7.7 g) at room temperature, and the mixture is stirred for 3 hours. The precipitated pyridine hydrochloride is filtered off, and the mother liquor is concentrated under reduced pressure. To the resulting oily residue is added water, and the mixture is extracted with chloroform. The organic layer is washed with water and saturated aqueous sodium chloride, dried over anhydrous sodium sulfate and the solvent is distilled off. The resulting solid is recrystallized from ethanol to give title compound (6.1 g) having the following physical properties.

m.p. 147°–148° C.

IR (KBr) $\nu$: 3460, 3425, 2950, 1750, 1735, 1695, 1620, 1560, 1530, 1485, 1450, 1385, 1295, 1225, 1175, 990, 830 cm$^{-1}$.

NMR (DMSO-$d_6$) $\delta$: 10.88 (1H, bs), 10.17 (1H, bs), 6.84 (1H, s), 5.83 (3H, s), 3.77 (3H, s), 3.70–3.15 (4H), 1.77–1.25 (6H).

Elementary analysis: Calcd.: C, 49.31; H, 5.24; N, 19.17 (%). Found: C, 49.20; H, 5.21; N, 19.23 (%).

EXAMPLE 7

Preparation of dimethyl 6-morpholinopyrimidine-2,4-dioxamate:

2,4-Diamino-6-morpholinopyrimidine (150 g) is suspended in anhydrous pyridine (2 liter) and thereto is added dropwise methyloxalyl chloride (160 ml) under ice cooling, and the mixture is stirred at room temperature for 3 hours. The precipitated pyridine hydrochloride is filtered off, and the mother liquor is concentrated under reduced pressure. The remaining solid is dissolved in chloroform and the mixture is washed with saturated aqueous sodium chloride and dried over anhydrous sodium sulfate. The solvent is distilled off, and the resulting solid is recrystallized from dioxane to give title compound (130 g) having the following physical properties.

m.p. 190°–193° C.

IR (KBr) $\nu$: 3420, 3350, 1720, 1620, 1560, 1520, 1430, 1310, 1280, 1215, 1165, 1120, 1040, 1015, 985, 905, 815, 740, 515 cm$^{-1}$.

NMR (CDCl$_3$) $\delta$: 9.45 (1H, bs), 9.05 (1H, bs), 7.23 (1H, s), 3.95 (6H, s), 3.80–3.50 (8H).

Elementary analysis: Calcd.: C, 45.78; H, 4.67; N, 19.07 (%). Found: C, 45.79; H, 4.68; N, 18.80 (%).

EXAMPLE 8

Preparation of diisopropyl 6-morpholinopyrimidine-2,4-dioxamate:

2,4-Diamino-6-morpholinopyrimidine (5.85 g) is dissolved in anhydrous pyridine (80 ml) and thereto is added dropwise isopropyloxalyl chloride (9 ml) at room temperature, and the mixture is stirred at room temperature for 3 hours. The precipitated pyridine hydrochloride is filtered off, and the mother liquor is concentrated under reduced pressure. The remaining solid is washed with ether and water to give crude crystal. The product is recrystallized from isopropyl alcohol to give title compound (3.92 g) having the following physical properties.

m.p. 183°–185° C.

IR (KBr) $\nu$: 3430, 3300, 3000, 1720, 1620, 1550, 1530, 1480, 1450, 1380, 1300, 1220, 1190, 1110, 1070, 1045, 1020, 980, 940, 905, 840, 825, 525 cm$^{-1}$.

Elementary analysis: Calcd.: C, 51.06; H, 5.95; N, 16.54 (%). Found: C, 50.81; H, 5.89; N, 16.39 (%).

EXAMPLE 9

Preparation of di-n-propyl 6-piperidinopyrimidine-2,4-dioxamate:

2,4-Diamino-6-piperidinopyrimidine (5.8 g) is dissolved in anhydrous pyridine (80 ml) and thereto is added dropwise n-propyloxalyl chloride (9.8 g) at room temperature, and the mixture is stirred at room temperature for 2 hours. The precipitated pyridine hydrochloride is filtered off, and the mother liquor is concentrated under reduced pressure. The remaining oily residue is dissolved in chloroform and the mixture is washed with saturated aqueous sodium chloride and dried over anhydrous sodium sulfate. The solvent is distilled off, and the resulting oily residue is dissolved in ethyl acetate and thereto is added ether. the precipitated solid is separated by filtration and recrystallized from ethanol to give title compound (6.3 g) having the following physical properties.

m.p. 97.4°–101.4° C.

IR (KBr) $\nu$: 3450, 3260, 2980, 2950, 2870, 1740, 1725, 1690, 1620, 1540, 1490, 1450, 1400, 1385, 1360, 1345, 1300, 1285, 1270, 1240, 1215, 1195, 1180, 1060, 1040, 1025, 985, 820 cm$^{-1}$.

NMR (DMSO-$d_6$) $\delta$: 10.88 (bs, 1H), 10.15 (bs, 1H), 6.95 (s, 1H), 4.18 (t, 2H), 4.12 (t, 2H), 3.65–3.20 (4H), 1.90–1.10 (10H), 0.94 (t, 3H), 0.84 (t, 3H)

Elementary analysis: Calcd.: C, 54.15; H, 6.46; N, 16.62 (%). Found: C, 54.36; H, 6.30; N, 16.77 (%).

EXAMPLE 10

Preparation of di-n-propyl 6-morpholinopyrimidine-2,4-dioxamate:

2,4-Diamino-6-morpholinopyrimidine (5.9 g) is dissolved in anhydrous pyridine (80 ml) and thereto is added dropwise n-propyloxalyl chloride (9.8 g) at room temperature, and the mixture is stirred at room temperature for 2 hours. The precipitated pyridine hydrochloride is filtered off, and the mother liquor is concentrated under reduced pressure. To the remaining oily residue are added ethyl acetate and ether to solidify the product. The solid is washed with ether and water to give crude crystal. The product is recrystallized from ethanol to give title compound (8.3 g) having the following physical properties.

m.p. 145°–146° C.

IR (KBr) $\nu$: 3325, 2970, 2930, 1735, 1720, 1685, 1605, 1560, 1520, 1440, 1410, 1370, 1295, 1280, 1215, 1170, 1105, 1070, 1025, 1000, 930, 885, 820, 715 cm$^{-1}$.

NMR (DMSO-$d_6$) $\delta$: 10.96 (bs, 1H), 10.26 (bs, 1H), 6.94 (s, 1H), 4.18 (t, 2H), 4.10 (t, 2H), 3.75–3.30 (8H), 1.64 (4H), 0.94 (t, 3H), 0.84 (t, 3H).

Elementary analysis: Calcd.: C, 51.06; H, 5.95; N, 16.54 (%). Found: C, 51.11; H, 5.79; N, 16.50 (%).

EXAMPLE 11

Preparation of dibenzyl 6-morpholinopyrimidine-2,4-dioxamate:

2,4-Diamino-6-morpholinopyrimidine (5.9 g) is dissolved in anhydrous pyridine (80 ml) and thereto is added dropwise benzyloxalyl chloride (12.3 g) at room temperature, and the mixture is stirred at room temperature for 2 hours. The precipitated pyridine hydrochloride is filtered off, and the mother liquor is concentrated under reduced pressure. The remaining oily residue is dissolved in chloroform and the mixture is washed with saturated aqueous sodium chloride and dried over anhydrous sodium sulfate. The solvent is distilled off, and the resulting solid is recrystallized from ethanol to give title compound (8.9 g) having the following physical properties.

m.p. 161°–163° C.

IR (KBr) $\nu$: 3450, 3200, 2980, 2855, 1760, 1615, 1540, 1510, 1480, 1445, 1385, 1370, 1310, 1255, 1215, 1195, 1165, 1110, 1060, 1015, 1005, 975, 940, 900, 810, 760, 755, 705, 690 cm$^{-1}$.

NMR (DMSO-$d_6$) $\delta$: 11.02 (bs, 1H), 10.37 (bs, 1H), 7.48–7.15 (10H), 6.94 (s, 1H), 5.29 (s, 2H), 5.24 (s, 2H), 3.80–3.20 (8H).

Elementary analysis: Calcd.: C, 60.11, H, 4.85; N, 13.48 (%). Found: C, 59.86; H, 4.89; N, 13.60 (%).

EXAMPLE 12

Preparation of dibenzyl 6-piperidinopyrimidine-2,4-dioxamate semihydrate:

2,4-Diamino-6-piperidinopyrimidine (5.8 g) is dissolved in anhydrous pyridine (80 ml) and thereto is added dropwise benzyloxalyl chloride (12.5 g) at room temperature, and the mixture is stirred at room temperature for 2 hours. The precipitated pyridine hydrochloride is filtered off, and the mother liquor is concentrated under reduced pressure. The remaining oily residue is dissolved in ethyl acetate. To the mixture is added ether, and the precipitated solid is separated by filtration and washed with ether and water to give crude crystal. The product is recrystallized from ethanol to give title compound (9.2 g) having the following physical properties.

m.p. 155°–159° C.

IR (KBr) $\nu$: 3450, 3250, 2950, 2865, 1765, 1725, 1685, 1620, 1550, 1515, 1490, 1460, 1380, 1315, 1285, 1265, 1215, 1195, 1175, 1025, 985, 950, 815, 760, 695 cm$^{-1}$.

NMR (DMSO-$d_6$) $\delta$: 10.96 (bs, 1H), 10.30 (bs, 1H), 7.46–7.15 (10H), 6.92 (s, 2H), 5.28 (s, 2H), 5.21 (s, 2H), 3.60–3.35 (4H), 1.68–1.30 (6H).

Elementary analysis: Calcd.: C, 61.59; H, 5.36; N, 13.30 (%). Found: C, 61.79; H, 5.22; N, 13.32 (%).

EXAMPLE 13

Preparation of dimethyl 6-homopiperidinopyrimidine-2,4-dioxamate:

2,4-Diamino-6-homopiperidinopyrimidine (6.2 g) is dissolved in anhydrous pyridine (80 ml) and thereto is added dropwise methyloxalyl chloride (5.8 ml) at room temperature, and the mixture is stirred at room temperature for 2 hours. The precipitated pyridine hydrochloride is filtered off, and the mother liquor is concentrated under reduced pressure. The remaining oily residue is dissolved in ethyl acetate. To the mixture is added ether, and the precipitated solid is separated by filtration and recrystallized from ethanol to give title compound (7.3 g) having the following physical properties.

m.p. 130°–135° C.

IR (KBr) $\nu$: 3430, 3290, 2960, 2880, 1750, 1730, 1700, 1625, 1555, 1535, 1445, 1395, 1375, 1305, 1215, 1180, 1050, 995, 990, 965, 825, 800 cm$^{-1}$.

NMR (DMSO-$d_6$) $\delta$: 10.84 (bs, 1H), 10.13 (bs, 1H), 6.82 (s, 1H), 3.80 (s, 3H), 3.75 (s, 3H), 3.65–3.25 (4H), 1.85–1.50 (8H).

Elementary analysis: Calcd.: C, 50.66; H, 5.58; N, 18.46 (%). Found: C, 50.78; H, 5.49; N, 18.41 (%).

EXAMPLE 14

Preparation of dimethyl 6-pyrrolidinopyrimidine-2,4-dioxamate:

2,4-Diamino-6-pyrrolidinopyrimidine (5.4 g) is dissolved in anhydrous pyridine (80 ml) and thereto is added dropwise methyloxalyl chloride (5.8 ml) at room temperature, and the mixture is stirred at room temperature for 2 hours. The precipitated pyridine hydrochloride is filtered off, and the mother liquor is concentrated under reduced pressure. The remaining oily residue is dissolved in chloroform and the mixture is washed with saturated aqueous sodium chloride and dried over anhydrous sodium sulfate. The solvent is distilled off, and the resulting solid is recrystallized from ethanol to give dimethyl 6-pyrrolidinopyrimidine-2,4-dioxaminate monoethanolate. The product is suspended in water and the mixture is boiled for 5 minutes, and the resulting product is separated by filtration to give title compound (7.2 g) having the following physical properties.

m.p. 161°-162° C.

IR (KBr) ν: 3650, 3490, 3430, 2975, 2880, 1735, 1715, 1690, 1615, 1565, 1555, 1530, 1485, 1450, 1375, 1355, 1340, 1310, 1280, 1250, 1235, 1210, 1175, 1045, 990, 920, 910, 820, 795 cm$^{-1}$.

NMR (DMSO-$d_6$) δ: 10.86 (bs, 1H), 10.10 (bs, 1H), 6.18 (s, 1H), 3.82 (s, 3H), 3.78 (s, 3H), 3.52-3.10 (4H), 2.10-1.70 (4H).

Elementary analysis: Calcd.: C, 47.86; H, 4.88; N, 19.93 (%). Found: C, 47.82; H, 4.76; N, 19.90 (%).

EXAMPLE 15

Preparation of diethyl 6-(4-methylpiperazino)pyrimidine-2,4-dioxamate:

2,4-Diamino-6-(4-methylpiperazino)pyrimidine (2.50 g) is dissolved in anhydrous pyridine (20 ml) and thereto is added dropwise ethyloxalyl chloride (3.61 g) at room temperature, and the mixture is stirred at room temperature for 2 hours. To the reaction mixture is added water, and the mixture is extracted with methylene chloride three times. The combined organic layers are washed with water and dried over anhydrous sodium sulfate, and the solvent is distilled off. The resulting solid is recrystallized from ethyl acetate-ethanol to give title compound (2.24 g) having the following physical properties.

m.p. 173°-175° C.

IR (KBr) ν: 3320, 2990, 2950, 2860, 2810, 1750, 1720, 1680, 1610, 1560, 1530, 1440, 1410, 1360, 1290, 1270, 1210, 1180, 1150, 1000, 820, 640 cm$^{-1}$.

Elementary analysis: Calcd.: C, 50.00; H, 5.92; N, 20.58 (%). Found: C, 50.14; H, 5.85; N, 20.65 (%).

EXAMPLE 16

Preparation of 6-piperidinopyrimidine-2,4-dioxamic acid hydrate:

Diethyl 6-piperidinopyrimidine-2,4-dioxamate (23.6 g) is suspended in water (500 ml) and thereto is added 1N sodium hydroxide solution (150 ml) under ice cooling, and the mixture is stirred for 20 minutes. To the mixture is added dropwise (0.2N hydrochloric acid (750 ml) under ice cooling, and the precipitated solid is separated by filtration, washed with water, and dried under reduced pressure to give a solid product (17.5 g). This product is dissolved in DMSO (80 ml) and undissolved materials are removed, and thereto is added methanol (1 liter) to precipitate white crystal. The product is separated by filtration and washed with methanol and then with water and dried to give title compound (10.9 g) having the following physical properties.

m.p. about 167° C. (decomp.)

IR (KBr) ν: 3460, 1660, 1600, 1560, 1450, 1370, 1250, 790, 755 cm$^{-1}$.

NMR (DMSO-$d_6$) δ: 10.60 (1H, bs), 9.90 (1H, bs), 7.00 (1H, s), 3.50 (4H, bs), 1.57 (6H, bs).

Elementary analysis (as trihydrate): Calcd.: C, 39.90; H, 5.41; N, 17.90 (%). Found: C, 39.66; H, 5.21; N, 18.20 (%).

EXAMPLE 17 Preparation of 6-morpholinopyrimidine-2,4-dioxamic acid hydrate:

Diethyl 6-morpholinopyrimidine-2,4-dioxamate (11.9 g) is suspended in water (250 ml) and thereto is added 1N sodium hydroxide solution (75 ml) under ice cooling, and the mixture is stirred for 20 minutes. To the mixture is added dropwise 1N hydrochloric acid (75 ml) under ice cooling, and the precipitated solid is separated by filtration, washed with water, and dried under reduced pressure to give a solid product (8.7 g). This product is dissolved in DMSO (40 ml) and undissolved materials are removed, and thereto is added methanol (500 ml) to precipitate white crystal. The product is separated by filtration and washed with methanol and then with water and dried to give title compound (6.9 g) having the following physical properties.

m.p. 186°-190° C. (decomp.)

IR (KBr) ν: 3450, 3240, 1725, 1675, 1605, 1565, 1455, 1365, 1255, 1150, 1110, 790, 755 cm$^{-1}$.

NMR (DMSO-$d_6$) δ: 10.70 (1H, bs), 9.95 (1H, bs), 7.00 (1H, s), 3.55 (8H, d).

Elementary analysis (as trihydrate): Calcd.: C, 36.64; H, 4.87; N, 17.81 (%). Found: C, 36.92; H, 4.75; N, 18.05 (%).

What is claimed is:

1. A pyrimidine compound of the formula:

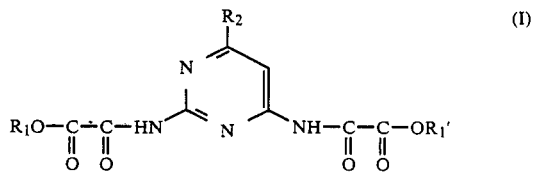

wherein $R_1$ and $R_1'$ are the same or different and are each hydrogen atom, a lower alkyl, benzyl, an alkali metal, or amonium; $R_2$ is hydrogen atom, a halogen atom, a lower alkyl, a lower alkoxy, an aryl, a group of the formula:

wherein $R_3$ and $R_4$ are the same or different and are each hydrogen atom, a lower alkyl, or an aryl, or a group of the formula:

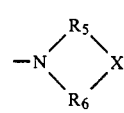

wherein $R_5$ and $R_6$ are the same or different and are each an alkylene having 1 to 3 carbon atoms, and X is oxygen atom, methylene, or a group of the formula:

>N—Y wherein Y is hydrogen atom, a lower alkyl, benzyl, or an aryl, or a hydrate thereof.

2. The compound according to claim 1, wherein $R_1$ and $R_1'$ are each hydrogen atom, methyl, ethyl, n-propyl, isopropyl, or benzyl, and $R_2$ is a group of the formula:

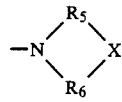

wherein $R_5$, $R_6$ and X are as defined in claim 1, or a hydrate thereof.

3. The compound according to claim 2, wherein $R_2$ is a member selected from the group consisting of piperidino, homopiperidino, pyrrolidino, morpholino, and 4-methylpiperazino.

4. A pharmaceutical composition for the prophylaxis and treatment of various allergic diseases, which comprises as an active ingredient a prophylactically or therapeutically effective amount of the pyrimidine compound as set forth in claim 1 in admixture with a conventional pharmaceutically acceptable carrier or diluent.

5. A pharmaceutical composition according to claim 4, wherein $R_1$ and $R_1'$ are each hydrogen atom, methyl, ethyl, n-propyl, isopropyl, or benzyl, and $R_2$ is a group of the formula:

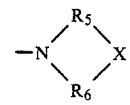

or a hydrate thereof.

6. A pharmaceutical composition according to claim 4, wherein $R_2$ is a member selected from the group consisting of piperidino, homopiperidino, pyrrolidino, morpholino, and 4-methylpiperazino.

* * * * *